United States Patent
Penenberg

(10) Patent No.: US 7,819,879 B2
(45) Date of Patent: Oct. 26, 2010

(54) GUIDE PIN PLACEMENT FOR HIP RESURFACING

(75) Inventor: Brad L. Penenberg, Beverly Hills, CA (US)

(73) Assignee: Wright Medical Technology, Inc., Arlington, TN (US)

( * ) Notice: Subject to any disclaimer, the term of this patent is extended or adjusted under 35 U.S.C. 154(b) by 501 days.

(21) Appl. No.: 11/738,183

(22) Filed: Apr. 20, 2007

(65) Prior Publication Data

US 2008/0021479 A1    Jan. 24, 2008

Related U.S. Application Data

(60) Provisional application No. 60/793,795, filed on Apr. 21, 2006.

(51) Int. Cl.
*A61B 17/58* (2006.01)
*A61B 17/60* (2006.01)
*A61F 2/00* (2006.01)

(52) U.S. Cl. ...................................... 606/96; 606/86 R

(58) Field of Classification Search .................. 606/59, 606/80, 87, 89, 91, 96, 98, 103, 104, 326, 606/329; 623/18.11, 19.12, 22.11, 22.12, 623/22.15, 23.11–23.14
See application file for complete search history.

(56) References Cited

U.S. PATENT DOCUMENTS

| 2,531,734 | A | * | 11/1950 | Hopkins | 606/97 |
| 2,785,673 | A | * | 3/1957 | Anderson | 623/23.11 |
| 3,704,707 | A | * | 12/1972 | Halloran | 606/97 |
| 4,383,527 | A | * | 5/1983 | Asnis et al. | 606/96 |
| 4,522,201 | A | | 6/1985 | Tongue | |
| D357,534 | S | * | 4/1995 | Hayes | D24/140 |
| 6,156,069 | A | * | 12/2000 | Amstutz | 623/22.11 |
| 6,755,865 | B2 | * | 6/2004 | Tarabishy | 623/22.12 |
| 6,869,434 | B2 | * | 3/2005 | Choi | 606/97 |
| 7,130,676 | B2 | * | 10/2006 | Barrick | 600/426 |
| 2003/0028196 | A1 | * | 2/2003 | Bonutti | 606/87 |
| 2003/0055431 | A1 | * | 3/2003 | Brannon | 606/80 |
| 2003/0130741 | A1 | * | 7/2003 | McMinn | 623/23.14 |
| 2003/0212405 | A1 | * | 11/2003 | Choi | 606/98 |
| 2005/0154398 | A1 | * | 7/2005 | Miniaci et al. | 606/96 |
| 2006/0184177 | A1 | * | 8/2006 | Echeverri | 606/91 |

* cited by examiner

*Primary Examiner*—Thomas C Barrett
*Assistant Examiner*—Larry E Waggle, Jr.
(74) *Attorney, Agent, or Firm*—Duane Morris LLP

(57) ABSTRACT

An instrument for guide pin placement in a femoral head and neck of a patient, the instrument having a reference pin guide member and a retrograde pin guide member adjustably attached to the reference pin guide member. The reference pin guide member has a bore configured for use in positioning and guiding an external reference pin. The retrograde pin guide member has a plurality of retrograde pin bores for use in positioning and guiding a retrograde reference pin into the femoral neck and head of the patient using a retrograde approach. If an initial retrograde reference pin is not positioned properly, one of the plurality of retrograde pin bores is used to insert another retrograde reference pin in a more desirable position using a retrograde approach.

10 Claims, 4 Drawing Sheets

GUIDE PIN PLACEMENT FOR HIP RESURFACING

CROSS REFERENCE TO RELATED APPLICATIONS

This application is a continuation of and claims priority to application Ser. No. 60/793,795, filed Apr. 21, 2006, which is pending.

STATEMENT REGARDING FEDERALLY SPONSORED RESEARCH OR DEVELOPMENT

Not applicable

FIELD OF THE INVENTION

The present invention relates to hip surgery, and more particularly to placement of pin guides for use in hip resurfacing.

BACKGROUND OF THE INVENTION

In conventional total hip arthroplasty, the head and neck of the natural femur are removed and replaced with an artificial femoral head and neck. The artificial head and neck are attached to a stem that is secured in the intramedullary canal of the femur. Over the years total hip arthroplasty has had excellent clinical success. However, various conditions can arise in which it becomes necessary to perform revision surgery on the hip joint. The presence of the implant in the femur can sometimes result in stress shielding, osteolysis or other conditions that lead to the gradual loss of bone stock and loosening of the implant. An infection may require removal of the implant. Additionally, the useful life of an artificial hip joint is about 15 to 25 years, and a young hip patient will therefore typically require a revision surgery at some point in his or her lifetime.

When performing a revision hip procedure, it is desirable to have as much bone stock available as possible. Accordingly, efforts have been made to develop surface replacement arthroplasty procedures that preserve bone stock in hip procedures. In surface replacement arthroplasty of the hip, the natural femoral head and neck are preserved, but are resurfaced to receive an artificial femoral head. An example of such a femoral head for use in surface replacement arthroplasty procedures is shown in FIGS. 1, 2, 7 and 8 of U.S. Pat. No. 6,156,069 (Amstutz), which is incorporated herein by reference. As shown in FIG. 1 of Amstutz, the femoral head includes a central tapered stem and a spherical surface replacement portion. An inner surface of the prosthesis covers the reamed bone of the femoral head, while the central tapered stem is centered in the femoral head and neck. Femoral heads of the type shown in Amstutz are available from Wright Medical Technology, Inc., 5677 Airline Road, Arlington, Tenn. 38002.

In one technique of surface replacement arthroplasty, the surfacing of the femoral head and the resulting positioning of the femoral component are based on the placement of a guide pin in the femoral neck and head. The surgeon opens the hip, dislocates the femur, and then centers the guide pin in the femoral head and neck using an antegrade approach. The guide pin protrudes from the femoral head, and is used to orient surfacing instruments. Amstutz provides views of a guide pin centered in the head and neck of a femur (FIGS. 9 and 10 of U.S. Pat. No. 6,153,069). Amstutz further describes instruments and techniques for accurate placement of the guide pin, along with use of the guide pin to surface the femoral head for receipt of the femoral implant.

Because surfacing of the femoral head is based on the position of the guide pin, accurate placement of the guide pin in the femoral head and neck is critical in surface replacement arthroplasty techniques such as those described in Amstutz. However, assessing the femoral head-neck relationship intra-operatively after dislocation and then placing the guide pin in an antegrade fashion can be somewhat complicated and unreliable. A relatively large exposure is required, particularly for inexperienced surgeons. A large exposure increases bleeding, pain and the risk of infection.

The present invention improves on prior art surface replacement arthroplasty by incorporating a retrograde approach for centering the guide pin. Retrograde approaches are used in hip fracture fixation using plates and a cannulated lag screw. A guide pin is placed retrograde into the desired position within the femoral neck and head. The procedure takes about ten minutes and is accomplished with the patient in a supine position using image guidance (i.e. C-arm). The guide pin is then used to place the cannulated lag screw. An example of one such femoral fracture fixation technique is discussed in U.S. Pat. No. 4,522,201 (Tongue).

Retrograde approaches have also been used to drive resurfacing instruments located in the hip via a driveshaft located in the femoral head and neck. The resurfacing instruments are introduced through a main incision, and are connected to the end of a driver that is inserted retrograde through a channel formed in the femoral head and neck. U.S. Patent Application Publication 2003/0028196 (Bonutti) teaches a technique for reaming the acetabulum using a drive shaft disposed in the femoral head and neck (see particularly FIGS. 68-73). U.K. Patent 2,372,302 (McMinn) teaches a similar technique for resurfacing the femoral head (see particularly FIGS. 4-6). As shown in FIG. 2 of McMinn, a guide-wire is inserted through the lateral aspect of the femur and up into the femoral head and neck, with the desired position obtained using either an external alignment jig, a navigation system, or x-ray control. Following insertion of the guide-wire, the femoral head is dislocated from the acetabulum. The guide-wire is then over-drilled, producing a canal, typically of 8.5 mm in diameter, up the femur, femoral neck, and exiting through the zenith of the femoral head. Once the canal has been completed, the drill is removed and preparation of the femoral head is then commenced. The first step in femoral head preparation, shown in FIG. 4 of McMinn, is the insertion of a drive rod up the canal in the femur. An appropriately sized sleeve cutter of generally hollow cup shape is inserted through the main incision and releasably secured to the end of the drive rod, which extends out of the top of the femoral head. The rod is driven by any suitable power means and the cutter advanced down onto the femoral head so that the periphery thereof is thus resected. The cutter is then unscrewed and removed via the main incision, with the drive rod being removed via the femoral neck incision. The next method step, shown in FIG. 5, involves the application of a sleeve resection guide to the periphery of the femoral head, with the guide being inserted through the main incision. An appropriate amount of zenith of the femoral head, as determined by the positioning of the guide, is then resected using a powered cutting blade, thereby maintaining the patient's correct leg length. After completion, the guide is removed through the main incision. The drive rod is then again inserted through the femoral neck incision and up along the canal so that the threaded end of the drive rod extends from the top of the resected femoral head. As indicated in FIG. 6 of McMinn, an appropriately sized chamfer cutter is then inserted through the main incision and attached to the end of the drive rod. The drive rod is moved down the canal so that the cutter is brought down onto the femoral head so that when the drive rod is powered to rotate, the cutter similarly rotates and cuts the femoral head to provide a chamfer thereon. Once the chamfering of the femoral head shown in FIG. 6 has been carried out, the femoral head preparation is complete.

Prior art techniques such as Bonutti and McMinn form a large hole in the lateral cortex and into the head and neck for direct retrograde access of cutting instruments. Such large holes may lead to fracture in the sub-trochanteric region. Additionally, the procedures are not done preoperatively, and do not provide teachings concerning the placement of guide pins for use in surface replacement arthoroscopy of the type described in Amstutz.

As far as the inventor is aware, retrograde approaches have not been used to center guide pins for use in surface replacement arthroplasty. There if thus a need for the novel approach for pin guide placement presented herein.

OBJECTS AND SUMMARY OF THE INVENTION

It is an object of the invention to provide a less invasive approach for establishing the position of a guide pin for use in a femoral resurfacing procedure.

It is an object of the invention to provide a retrograde approach for establishing the position of a guide pin for use in a femoral resurfacing procedure.

It is an object of the invention to provide guide pin placement instruments and procedures that reduce exposure, risk of mal-alignment, soft tissue trauma, bleeding, pain, time of recovery and other factors associated with total or partial hip resurfacing.

The objects and advantages of the invention are achieved by providing an instrument for guide pin placement in a femoral head and a femoral neck of a patient, the instrument comprising generally a reference pin guide member and a retrograde pin guide member adjustably attached to the reference pin guide member. The reference guide pin member has a bore configured for use in positioning and guiding an external reference pin. The retrograde pin guide member is used to position and guide a retrograde reference pin. The retrograde pin guide member has a plurality of retrograde pin bores positioned and configured for use in positioning and guiding a retrograde reference pin into the femoral neck and the femoral head of the patient using a retrograde approach. The adjustable attachment is configured to provide selective adjustment and setting of a position of the external reference pin and the retrograde reference pin relative to one another.

The plurality of pin bores are preferably distributed on the retrograde pin guide member such that the pin bores are spaced apart by a substantially uniform distance from adjacent ones of the pin bores. In one embodiment, the pin bores are fixed in parallel to one another.

The adjustable attachment preferably includes an up-down adjustment means and/or a rotational adjustment means. The up-down and rotational adjustment means can be provided by a rod member slidingly engaged in a sleeve member, and a selective locking means for selectively locking the rod member in a set position relative to the sleeve member. In one embodiment, the sleeve member depends downward from the reference guide pin member and the rod member extends upward from the retrograde guide pin member. The adjustable attachment can include a flexion-extension adjustment means, the flexion-extension adjustment means being positioned between the retrograde guide pin member and the rod member to allow selection of a flexion-extension orientation of the retrograde pin guide member. The flexion-extension means is can be a universal joint. A flexion-extension locking means can be provided for use in selectively locking the retrograde pin guide member in a selected position relative to the instrument.

Methods of setting a guide pin in a femoral neck of a patient for use in resurfacing a femoral head in a hip procedure are also provided. In one embodiment, a retrograde reference pin is inserted into the femoral neck from a retrograde approach until a distal end of the retrograde reference pin pierces a femoral cortex of the femur, thus forming a guide pin track in the femoral neck and a guide pin opening through the femoral cortex. The retrograde reference pin is removed from the femur to thereby expose the guide pin track and the guide pin opening. The guide pin opening is located, and a definitive guide pin is inserted antegrade through the guide pin opening and into the guide pin track. The definitive guide pin is used to resurface the femoral head.

Before inserting the retrograde reference pin, an external reference pin can be laid along an exterior of the patient in general alignment with the femoral neck for use as a varus-valgus reference guide during formation of the guide pin track. The external reference pin, femoral neck and femoral head are viewed under external imaging in order to determine a desired location of the guide pin track. The external reference pin as a varus-valgus reference guide during formation of the guide pin track.

After forming the guide pin track, the position of the retrograde reference pin in the femoral neck is studied under external imaging in order to verify whether the guide pin track is properly oriented. If the guide pin track is not properly oriented, a second retrograde reference pin is inserted into the femoral neck from a retrograde approach until a distal end of the second retrograde reference pin pierces a femoral cortex of the femur to thereby form a second guide pin track in the femoral neck and a second guide pin opening through the femoral cortex.

The retrograde reference pin can be inserted before opening the hip of the patient, while the step of inserting the definitive guide pin into the guide pin track occurs after opening and dislocating the hip of the patient. The opening of the hip is preferably accomplished through a minimal incision of about 8 cm or less.

In total or partial hip resurfacing, it is desirable to use a retrograde approach to centering the guide pin because once the center of the neck has been established, the operation is much easier. By using the techniques described herein to shoot a pin through the lateral femoral cortex of the femur under fluoro, a surgeon is able to find the neck easily in two planes.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
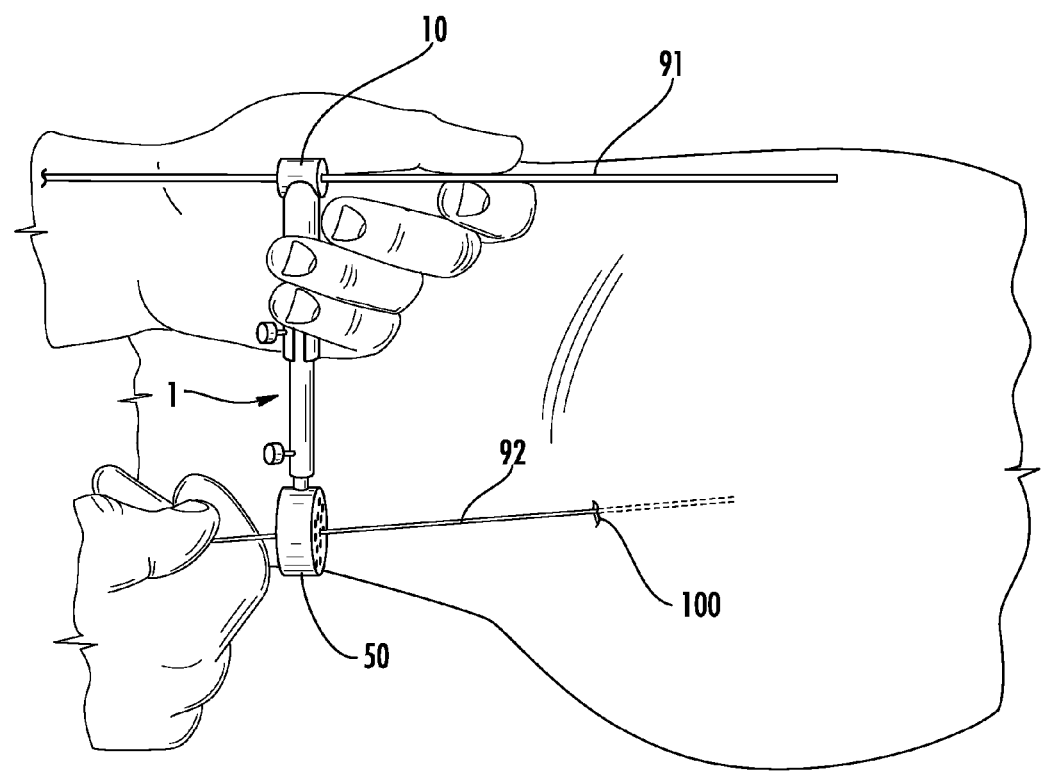
FIG. 1 is a front-side perspective view of one preferred embodiment of a method of centering a guide pin according to the invention.
Figure 2:
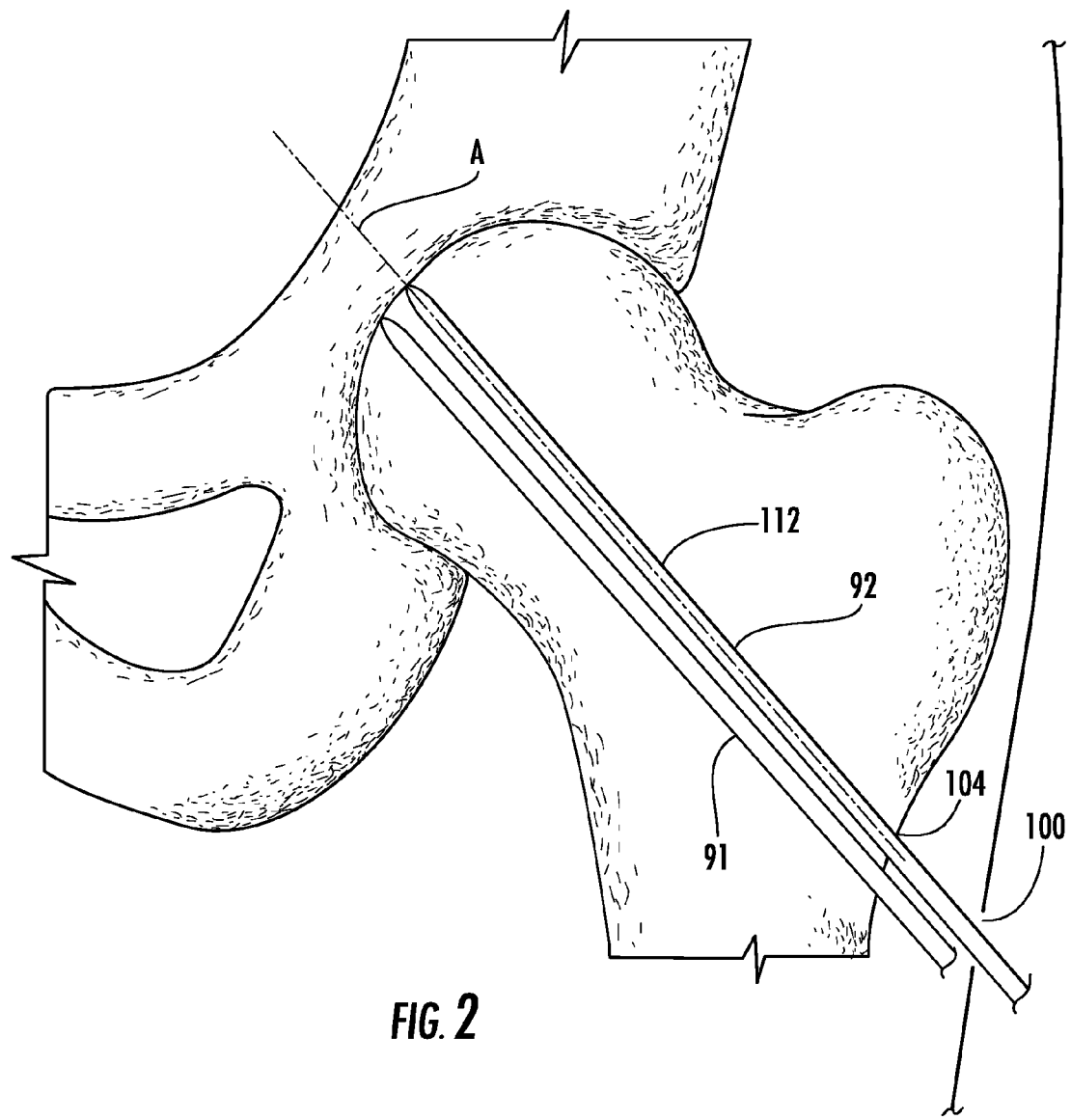
FIG. 2 is a fluoroscopy view of a method of centering a guide pin according to the invention.
Figure 3:
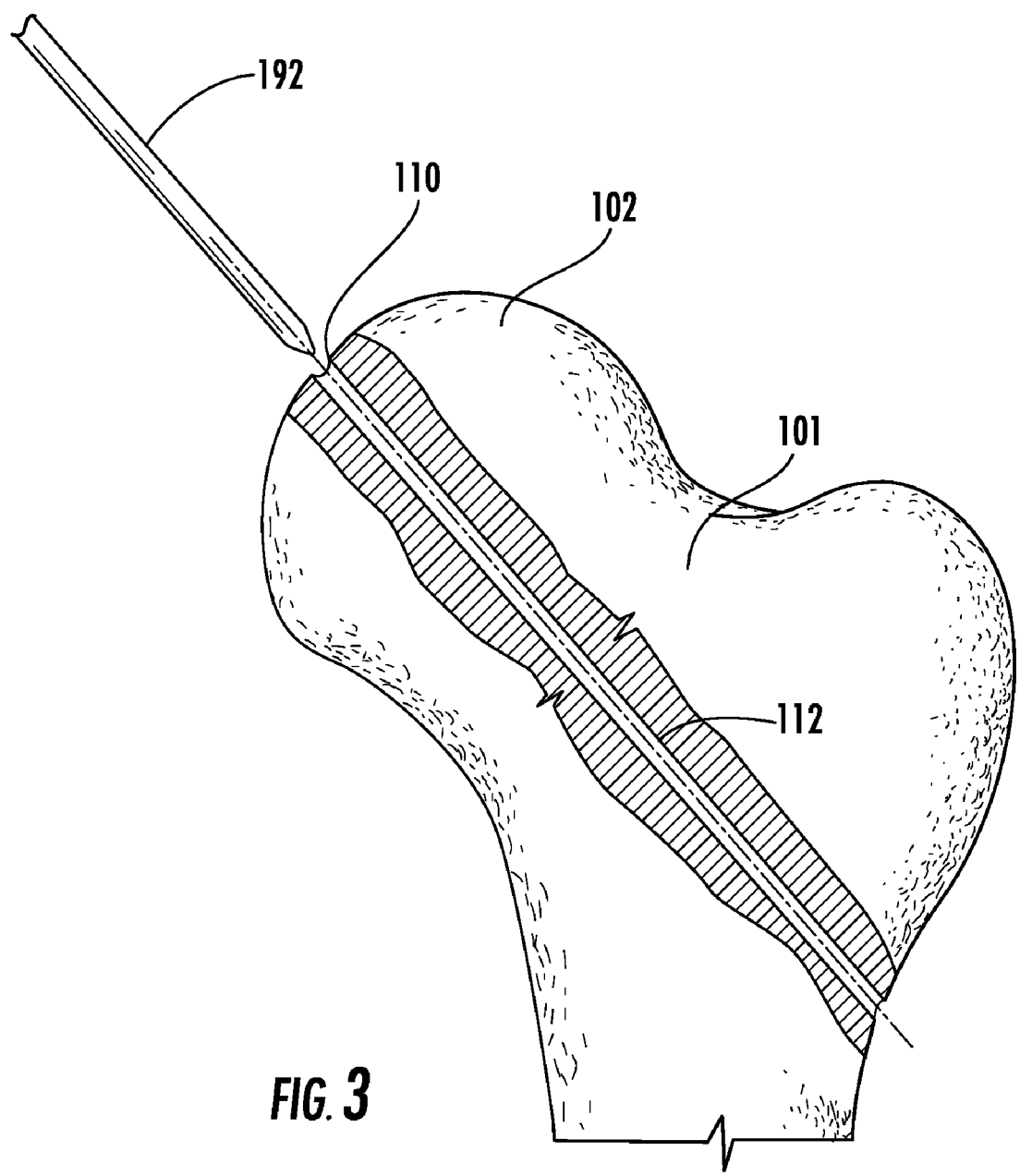
FIG. 3 is a representative view of use of a guide pin opening and track to establish a definitive guide pin in the head and neck of the femur.

As shown in FIGS. 1-4, the invention provides methods and instruments for precise positioning of a guide pin for use in resurfacing a femoral head and neck. As will be described in further detail below, internal imaging (currently, CRM or fluoroscopy images) and a retrograde approach are used to select and establish the position of a guide pin track 112 in the femoral head 102 and neck 101 prior to opening the hip. As indicated in FIG. 3, the hip is then opened (preferably using a minimally invasive approach, such as an incision of 8 cm or less), a definitive guide pin 192 is inserted antegrade into the guide pin track 112, and the definitive guide pin 192 is used to carry out the resurfacing procedure. A2

Figure 4:
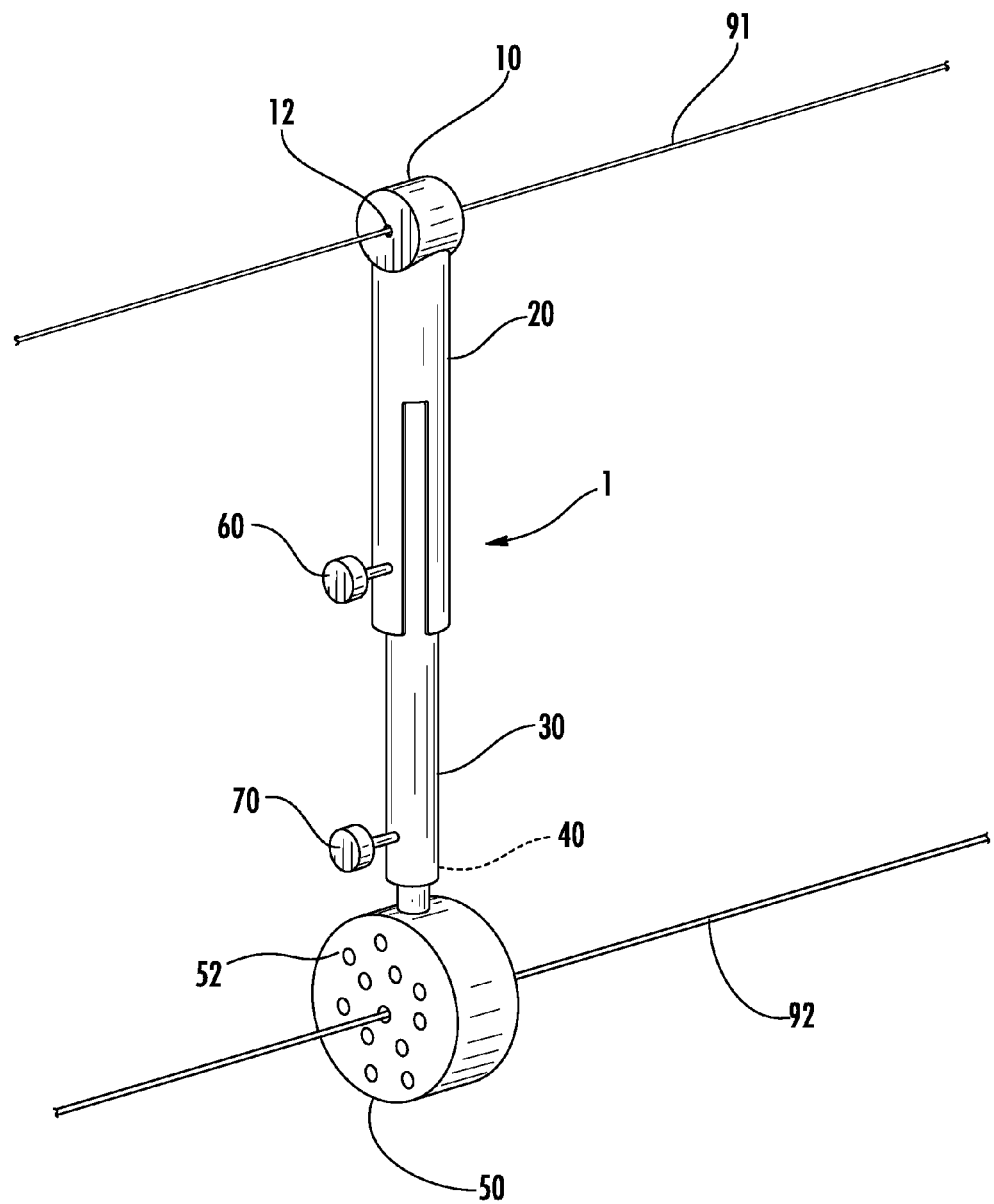
FIG. 4 is a preferred embodiment of one guide pin placement instrument of the invention.

FIGS. 1 and 4 show one embodiment of a preferred guide pin placement instrument 1 for use in carrying out the procedures described herein. The instrument 1 features a reference pin guide member 10 having a reference pin bore 12 for use in positioning and guiding an external reference pin 91 and a retrograde pin guide member 50 for positioning and guiding a retrograde reference pin 92. The guide pin placement instrument 1 is preferably provided with adjustment mechanisms that allow for selective adjustment and setting of the position of the external reference pin 91 and the retrograde reference pin 92 relative to one another. The adjustment mechanisms allow the instrument 1 to accommodate patients of various sizes, and also provide for fine-tuning the position of the external reference pin 91 and retrograde reference pin 92. Adjustments preferably include up/down, rotation (varus/valgus), and flexion/extension. In the embodiment shown in FIG. 4, up/down and rotational adjustments are provided by a rod member 30 slidingly engaged in a sleeve member 20. A selective locking means 60, such as a set screw 60, is provided for selectively locking the rod member 30 in a set position relative to the sleeve member 20. The position of the retrograde reference pin 92 is adjusted upward (anteriorly) relative to the external reference pin 91 by sliding the rod member 30 further into the sleeve member 20, and is likewise adjusted downward (posteriorly) by sliding the rod member 30 in the opposite direction. Rotating the rod member 30 within the sleeve 20 allows for rotational varus/valgus adjustment of the retrograde reference pin 92. As discussed in further detail below, the varus/valgus adjustment of the retrograde reference pin 92 is preferably made with reference to the external reference pin 91 while working under external imaging. When a desired position is attained, the set screw 60 is threaded down to lock the rod member 30 in position in the sleeve member 20. In the embodiment shown in FIG. 4, the sleeve member 20 depends downward from the reference pin guide member 10 while the rod member 30 extends upward from the retrograde guide pin member 50. However, the orientation of the rod 30 and sleeve 20 members could be reversed.

In the instrument 1 embodiment shown in FIG. 4, flexion/extension adjustment is provided by a flexion-extension adjustment means 40 that is positioned between the retrograde guide pin member 50 and the rod member 30. The flexion-extension adjustment means 40 allows the surgeons to select the flexion-extension orientation of the retrograde pin guide member 50, and thereby fine-tune the orientation of the retrograde reference pin 92. In a preferred embodiment, the flexion-extension adjustment means 40 is a universal joint, such that adjustments can be made in all dimensions. The simplest form of universal joint would be a ball-and-socket joint. Alternatively, the flexion-extension means 40 can be a hinge joint, such that adjustments can be made only in one plane. A flexion-extension locking means 70, such as a set screw 70, is preferably provided for selectively locking the retrograde pin guide member 50 in a selected position relative to the instrument 1. A3

As shown in FIG. 4, a preferred embodiment of a guide pin placement instrument 1 features a retrograde pin guide member 50 that has a plurality of pin bores 52. The various pin bores 52 are sized to closely but slidingly receive retrograde reference pins 92. As will be described in further detail below, the plurality of pin bores 52 are provided for use in guiding placement of a second retrograde reference pin 92, and are used in situations where the surgeon is not satisfied with the orientation of the first retrograde reference pin 92. Using the first retrograde reference pin 92 as a reference, a correction, i.e. a change in orientation of the guide pin track 112 (preferably in only one plane), can be effected by choosing a second retrograde pin bore 52 in the retrograde pin guide member 50 and, if necessary, readjusting the instrument 1 to obtain the necessary correction. The various pin bores 52 are preferably spaced a uniform distance from adjacent pin bores 52, such as 2 mm, 3 mm or 4 mm apart. The pin bores 52 are also preferably set at the same angle relative to one another, i.e. with axes in parallel. By referencing the retrograde pin bore 52 of the first retrograde reference pin 92, the surgeon can readily select an alternate retrograde pin bore 52 that is likely to provide a more desirable (typically, more centered) orientation. Alternatively, the retrograde pin guide member 50 can be provided with a single bore in the manner of the reference pin guide member 10, in which case it would be necessary to readjust the instrument 1 in order to position a second retrograde reference pin 92. Thus, one advantage of the instrument 1 shown in FIGS. 1 and 4 is that it eliminates or minimizes the need to readjust the position of the reference pin guide member 10.

FIG. 1 shows an external view of the surgical technique of the invention. In general, the surgeon uses the anterior external reference pin 91 and external imaging (e.g. fluoroscopy) in order to center the retrograde reference pin 92 as closely as possible to the plane of the center of the femoral neck 101. The surgeon initiates the procedure by palpating the greater trochanter in order to establish the location of the stab wound or opening 100. As indicated in FIGS. 1 and 2, the location of the stab wound 100 is distal to the greater trochanter so as to provide access to the lateral cortex 104 of the femur. Once the location of the stab wound is determined, a stab wound 100 is made at the selected location.

After making the stab wound 100, the surgeon orients the instrument 1 in the manner shown in FIG. 1, with the external reference pin 91 resting anteriorly on the skin of the patient. As indicated in FIG. 1, the stab wound 100 defines the entry point of the retrograde reference pin 92, and therefore also sets the general position of the external reference pin 91. The distal end of the external reference pin 91 will typically rest in the frontal groin area of the patient. As shown in the imaging/fluoroscopy view of FIG. 2, positioning the external reference pin 91 at this location and in general alignment with the retrograde reference pin 92 allows the external reference pin 91 to serve as a varus-valgus reference guide during formation of the guide pin track 112 under fluoroscopy.

As indicated in FIG. 2, the target for entry of the retrograde reference pin 92 is on the lateral cortex 104 distal to the greater trochanter. Accurate placement of the guide pin is critical in hip resurfacing procedures. In prior art resurfacing procedures, surgeons (particularly inexperienced surgeons) require a large exposure of the femoral head and neck. With the technique of the present invention, it is easy even for inexperienced surgeons to identify the target location based on external palpitation of the greater trochanter external anatomy. Thus, the invention improves accuracy of guide pin placement while also allowing for reduction of exposure, which in turn reduces bleeding, pain, and risk of infection.

With the instrument positioned as shown in FIG. 1, the surgeon views the femoral head 102 and neck 101 under fluoroscopy (or such alternative imaging systems as may be available or developed in the future) in order to determine the desired location of the guide pin track 112. As shown in FIG. 2, the external reference pin 91 is used as a guide to identify the proper varus/valgus angle for the guide pin track 112. As indicated in FIGS. 2 and 3, the preferred position of the guide pin track 112 is in the center or axis A of the femoral neck 101. However, any desired position, e.g. additional valgus, can be selected during percutaneous pin placement. A preferred angle is about 140 degrees.

Working under fluoroscopy, the surgeon then drills the retrograde reference pin 92 through the lateral femoral cortex and through the neck 101 along the selected path of the guide pin track 112 until the distal end of the retrograde reference pin 92 penetrates the surface of the femoral head 102, leaving a guide pin opening 110 on the femoral head 102. The retrograde reference pin 92 preferably has a diameter of 2 to 3 mm, a size that is sufficient to leave a visible hole 110 on the surface of the femoral head 102. The location of the guide pin hole 110 is preferably about 12 mm above the fovea.

The position of the retrograde reference pin 92 is then studied under fluoroscopy to verify whether the guide pin track 112 is properly oriented. If properly oriented, the retrograde reference pin 92 is then removed from the femur via the stab wound 100.

If fluoroscopy shows that the retrograde reference pin 92 is not sufficiently centered, a second guide pin track 112 can be formed. The guide pin placement instrument 1 shown in FIG. 4 assists in selecting a better orientation for the second guide pin track 112. Preferably prior to fully removing the first retrograde reference pin 92, an adjacent retrograde pin bore 52 is selected, i.e. a hole that is likely to provide a better centering. A second retrograde reference pin 92 is passed through the selected second retrograde pin bore 52. The relative position of the first and second retrograde pin bores 52 in the retrograde pin guide member 50 maintains an offset between the second retrograde reference pin 92 and the first retrograde reference pin 92, and thus directs the pin 92 into the femoral neck 101 along the desired path of the guide pin track 112.

Once the guide pin track 112 is properly oriented, the retrograde reference pin 92 is removed. The hip is then opened and dislocated in a standard manner. As indicated in FIG. 3, upon exposing the hip, the guide pin hole 110 can be readily identified as a small hole on the surface 110 of the femoral head 102. In prior art resurfacing procedures, surgeons (particularly inexperienced surgeons) required a large exposure of the femoral head and neck. With the technique of the present invention, it is easy even for inexperienced surgeons to identify the target location based on external palpitation of the greater trochanter external anatomy. Thus, the invention improves accuracy of guide pin placement while also allowing for reduction of exposure, which in turn reduces bleeding, pain, and risk of infection.

As shown in FIG. 3, once the guide pin hole 110 has been identified, a standard guide pin 192 (e.g., ⅜ inch Steinmann pin) can be readily inserted through the hole/guide pin opening 110 and installed in the guide pin track 112 through blunt insertion. Once the guide pin 192 is lodged in the guide pin track 112, the guide pin 192 can be used for any femoral head arthroplasty procedure that uses a guide pin, such as, for example, the procedure disclosed in U.S. Pat. No. 6,156,069 (Amstutz). The stab wound 100 can be used for a drain at the end of the surgical procedure. Unlike prior art procedures, there is no need to expose the area around the femoral neck 101. The guide pin track 112 assures that the guide pin 192 is properly centered in the femoral neck 101. If desired, the procedure for inserting the retrograde guide pin 92 and establishing the guide pin track 112 can be performed the day before the operation, since it is not necessary to open the hip in order to perform this portion of the procedure.

Advantages of the procedure include precise pin placement without the difficulties associated with prior art procedures. Less exposure is required than with procedures that use prior art neck gauges. Less exposure is of course desirable in MIS techniques. The technique assures ideal positioning of the femoral prosthesis with minimal soft tissue trauma, such as might occur using the traditional approach of directly visualizing the cortical surfaces of the femoral neck. This reduces the likelihood of compromising blood supply, reduces bleeding, and reduces post-operative pain. The procedure can significantly shorten the duration of the procedure. Because radiologic confirmation is obtained in each case, the risk of mal-alignment is significantly reduced. The foregoing factors can accelerate recovery by the patient.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A method of setting a guide pin in a femoral neck of a patient for use in resurfacing a femoral head in a hip procedure, comprising:

inserting a retrograde reference pin into the femoral neck from a retrograde approach until a distal end of said retrograde reference pin pierces a femoral cortex of the femoral head to thereby form a guide pin track in the femoral neck and a guide pin opening through the femoral cortex of the femoral head, the retrograde reference pin guided by a retrograde pin guide member having a plurality of retrograde pin bores extending through the retrograde in guide member, the plurality of retrograde pin bores configured for use in positioning and guiding the retrograde reference pin, at least two of the plurality of retrograde pin bores defining axes that are parallel with one another, the retrograde pin guide member adjustably attached to a reference pin guide member;

removing said retrograde reference pin from the femur to thereby expose said guide pin track and said guide pin opening, locating said guide pin opening, inserting a definitive guide pin antegrade through said guide pin opening and into the guide pin track, and using said definitive guide pin to resurface the femoral head.

2. The method of claim 1, further comprising, prior to said step of inserting said retrograde reference pin,
- laying an external reference pin along an exterior of the patient in general alignment with the femoral neck for use as a varus-valgus reference guide during formation of said guide pin track,
- viewing said external reference pin, the femoral neck and the femoral head under external imaging in order to determine a desired location of said guide pin track, and
- using said external reference pin as a varus-valgus reference guide during formation of said guide pin track.

3. The method of claim 1, further comprising, after forming said guide pin track,
- studying the position of the retrograde reference pin in the femoral neck under external imaging to verify whether said guide pin track is properly oriented, and
- if said guide pin track is not properly oriented, inserting a second retrograde reference pin into the femoral neck from a retrograde approach until a distal end of said second retrograde reference pin pierces a femoral cortex of the femur to thereby form a second guide pin track in the femoral neck and a second guide pin opening through the femoral cortex.

4. The method of claim 1, wherein said step of inserting said retrograde reference pin occurs before opening the hip of the patient, and said step of inserting said definitive guide pin into the guide pin track occurs after opening and dislocating the hip of the patient.

5. The method of claim 4, wherein said opening of the hip is accomplished through a minimal incision of about 8 cm or less.

6. A method of setting a guide pin in a femoral neck of a patient for use in resurfacing a femoral head in a hip procedure, comprising:
- providing an instrument for guide pin placement in the femoral head and the femoral neck of the patient, said instrument comprising:
  - a reference pin guide member having a bore configured for use in positioning and guiding an external reference pin,
  - a retrograde pin guide member for use in positioning and guiding a retrograde reference pin, said retrograde pin guide member having a plurality of retrograde pin bores extending through the retrograde pin guide member, the plurality of retrograde pin bores positioned and configured for use in positioning and guiding a retrograde reference pin into the femoral neck and the femoral head of the patient using a retrograde approach, at least two of the plurality of retrograde pin bores defining axes that are parallel with one another, and
  - said retrograde pin guide member adjustably attached to said reference pin guide member, said adjustable attachment configured to provide selective adjustment and setting of a position of said external reference pin and said retrograde reference pin relative to one another;
- inserting an external reference pin into said bore of said reference pin guide member;
- inserting a retrograde reference pin into a selected one of said plurality of retrograde pin bores;
- laying said external reference pin along an exterior of the patient in general alignment with the femoral neck for use as a varus-valgus reference guide during formation of said guide pin track;
- viewing said external reference pin and the femoral neck under external imaging in order to determine a desired location of a guide pin track; and
- inserting a retrograde reference pin into the femoral neck from a retrograde approach until a distal end of said retrograde reference pin pierces a femoral cortex of the femoral head to thereby form a guide pin track in the femoral neck and a guide pin opening through the femoral cortex of the femoral head, wherein said step of inserting said retrograde reference pin includes using said retrograde reference pin as a varus-valgus reference guide during formation of said guide pin track.

7. The method of claim 6, further comprising
- removing said retrograde reference pin from the femur to thereby expose said guide pin track and said guide pin opening;
- locating said guide pin opening;
- inserting a definitive guide pin antegrade through said guide pin opening and into said guide pin track; and
- using said definitive guide pin to resurface the femoral head.

8. The method of claim 6, further comprising, after forming said guide pin track,
- studying the position of the retrograde reference pin in the femoral neck under external imaging to verify whether said guide pin track is oriented in an acceptable position, and
- if said guide pin track is not oriented in an acceptable position, selecting a second pin bore from said plurality of pin bores of said guide pin placement instrument, wherein said second pin bore is selected on the basis of being likely to provide a more acceptable position for said guide pin track than said retrograde reference pin;
- inserting a second retrograde reference pin into said second selected retrograde pin bore;
- inserting said second retrograde reference pin into the femoral neck from a retrograde approach until a distal end of said second retrograde reference pin pierces a femoral cortex of the femur to thereby form a second guide pin track in the femoral neck and a second guide pin opening through the femoral cortex, said retrograde pin guide member maintaining an offset between said second retrograde reference pin and said first retrograde reference pin during insertion of said second retrograde reference pin.

9. The method of claim 8, further comprising
- removing said retrograde reference pin and said second retrograde reference pin from the femur to thereby expose said guide pin tracks and said guide pin openings;
- locating said second guide pin opening;
- inserting a definitive guide pin antegrade through said second guide pin opening and into said second guide pin track; and
- using said definitive guide pin to resurface the femoral head.

10. The method of claim 6, wherein said opening of the hip is accomplished through a minimal incision of about 8 cm or less.

* * * * *